United States Patent
Iaquaniello et al.

(10) Patent No.: US 9,701,535 B2
(45) Date of Patent: Jul. 11, 2017

(54) PROCESS FOR PRODUCING A SYNGAS INTERMEDIATE SUITABLE FOR THE PRODUCTION OF HYDROGEN

(75) Inventors: Gaetano Iaquaniello, Rome (IT); Barbara Cucchiella, Rome (IT); Elena Antonetti, Rome (IT)

(73) Assignee: STAMICARBON B.V., Sittard (NL)

(*) Notice: Subject to any disclaimer, the term of this patent is extended or adjusted under 35 U.S.C. 154(b) by 5 days.

(21) Appl. No.: 14/123,030

(22) PCT Filed: Jun. 25, 2012

(86) PCT No.: PCT/NL2012/050443
§ 371 (c)(1),
(2), (4) Date: Dec. 30, 2013

(87) PCT Pub. No.: WO2012/177136
PCT Pub. Date: Dec. 27, 2012

(65) Prior Publication Data
US 2014/0103260 A1    Apr. 17, 2014

(30) Foreign Application Priority Data
Jun. 23, 2011   (EP) ...................................... 11171172

(51) Int. Cl.
*C01B 3/26*    (2006.01)
*C01B 3/38*    (2006.01)
(Continued)

(52) U.S. Cl.
CPC ................ *C01B 3/26* (2013.01); *C01B 3/386* (2013.01); *C01B 3/48* (2013.01); *C01B 3/50* (2013.01);
(Continued)

(58) Field of Classification Search
CPC ....................................................... C01B 31/20
See application file for complete search history.

(56) References Cited

U.S. PATENT DOCUMENTS

2002/0155061 A1    10/2002    Prasad et al.
2005/0268554 A1*   12/2005    Liu ........................ B01J 8/0453
                                                                                    48/61
(Continued)

FOREIGN PATENT DOCUMENTS

EP    640559    3/1995
EP    1 433 746    6/2004
(Continued)

OTHER PUBLICATIONS

International Search Report for PCT/NL2012/050443, mailed Aug. 29, 2012, 3 pages.
(Continued)

*Primary Examiner* — Melvin C Mayes
*Assistant Examiner* — Kenneth Vaden
(74) *Attorney, Agent, or Firm* — Morrison & Foerster LLP

(57) ABSTRACT

Disclosed is a process for the production of a syngas mixture by catalytic partial oxidation. The syngas mixture is suitable as an intermediate in the production of hydrogen. According to the invention, the syngas is cooled, prior to a water gas shift reaction, with liquid water. This has the advantage of avoiding the problem of metal dusting, and it presents a gas mixture comprising water vapor that is particularly suitable for a water gas shift reaction in the production of hydrogen.

6 Claims, 2 Drawing Sheets

(51) Int. Cl.
*C01B 3/48* (2006.01)
*C07C 273/04* (2006.01)
*C01B 3/50* (2006.01)

(52) U.S. Cl.
CPC .... *C07C 273/04* (2013.01); *C01B 2203/0261* (2013.01); *C01B 2203/0475* (2013.01); *C01B 2203/068* (2013.01); *C01B 2203/0877* (2013.01); *C01B 2203/1241* (2013.01)

(56) References Cited

U.S. PATENT DOCUMENTS

| | | | |
|---|---|---|---|
| 2006/0064931 A1 | 3/2006 | Gary et al. | |
| 2008/0069765 A1 | 3/2008 | Jiang et al. | |
| 2008/0141951 A1* | 6/2008 | Liu | 122/18.2 |
| 2010/0063321 A1* | 3/2010 | Zardi et al. | 564/71 |

FOREIGN PATENT DOCUMENTS

| | | |
|---|---|---|
| EP | 1 903 001 | 3/2008 |
| FR | 2 848 548 | 6/2004 |
| WO | WO-97/37929 | 10/1997 |
| WO | WO-00/00426 | 1/2000 |
| WO | WO-01/32556 | 5/2001 |
| WO | WO-01/36323 | 5/2001 |
| WO | WO 03/080503 * | 10/2003 |
| WO | WO-2009/043365 A1 | 4/2009 |
| WO | WO-2010/144544 | 12/2010 |

OTHER PUBLICATIONS

Basini et al., "Catalytic partial oxidation of natural gas at elevated pressure and low residence time," Catalysis Today (2001) 64:9-20.
Basini, "Fuel rich catalytic combustion: Principles and technological developments in short contact time (SCT) catalytic processes," Catalysis Today (2006) 117:384-393.
Hickman and Schmidt, "Production of syngas by direct catalytic oxidation of methane," Science (1993) 259:343-346.
Hickman and Schmidt, "Synthesis gas formation by direct oxidation of methane over Pt monoliths," J Catalysis (1992) 138:267-282.
International Preliminary Report on Patentabilty and Written Opinion for PCT/NL2012/050443, issued Dec. 23, 2013, 6 pages.

* cited by examiner

PROCESS FOR PRODUCING A SYNGAS INTERMEDIATE SUITABLE FOR THE PRODUCTION OF HYDROGEN

CROSS-REFERENCE TO RELATED APPLICATIONS

This application is the national phase of PCT application PCT/NL2012/050443 having an international filing date of 25 Jun. 2012, which claims benefit of European application No. 11171172.7, filed 23 Jun. 2011. The contents of the above patent applications are incorporated by reference herein in their entirety.

FIELD OF THE INVENTION

The invention pertains to a process for the production of syngas by means of catalytic partial oxidation. In another aspect the invention relates to a method of making ammonia and/or urea using the syngas obtained by the process. In yet another aspect the method relates to a method for producing hydrogen.

BACKGROUND OF THE INVENTION

Syngas (which is a short for "synthesis gas") comprises carbon monoxide (CO) and hydrogen ($H_2$), and is an important source for the production of $H_2$. The conventional industrial process for producing syngas on an industrial scale is steam reforming, whereby a carbonaceous material is reacted with water in the form of steam. Another process, of increasing importance, involves subjecting the carbonaceous material to Catalytic Partial Oxidation. The present invention pertains to a process of this type, referred to hereinafter as "CPO process."

A typical CPO process, used for producing $H_2$, a carbonaceous material is subjected to catalytic partial oxidation, after which steam is added and a water gas shift reaction is allowed to take place. In this water gas shift reaction, carbon monoxide reacts with water so as to form carbon dioxide and hydrogen. The CPO reaction being exothermic, heat is produced. At the outlet temperatures of the CPO a corrosion problem called "metal dusting." may appear. Metal dusting is a catastrophic form of corrosion that occurs when susceptible materials are exposed to environments with high carbon activities. The corrosion manifests itself as a breakup of bulk metal to metal powder. This may shorten the life of the equipment involved, and may lead to contamination problems in end-product obtained from such equipment. Metal dusting for any given material tends to occur in a relatively narrow range (100-300° C.) of a temperature regime from 400 to 900° C. The particular temperature window of susceptibility depends on the material, gas composition, thermodynamic consideration and kinetics. In the case of the typical syngas composition the critical range of temperature is within 450-750° C.

It is believed that the phenomenon of metal dusting in syngas service is caused by the precipitation of carbon into the metals that comprise the material of construction. The mechanism underlying the metal dusting phenomenon is not completely understood, but it is known that the higher concentration of CO in the gas exiting the CPO reactor compared to a steam reforming reactor worsens the metal dusting phenomenon.

The latter phenomenon particularly occurs downstream of the CPO reactor, where the initial syngas mixture is subjected to cooling prior to the water gas shift reaction. As a result of the cooling, the gas passes the temperature range in which metal dusting is bound to occur. The temperature reduction is generally achieved in a Process Gas Boiler (PGB), which is a heat exchanger designed to quickly reduce the temperature of the process gas to a temperature suitable for the water gas shift reaction. Thus, also the PGB should be protected from metal dusting. A known method to reduce this phenomenon is to design the process gas boiler for a minimum residence time, preferably less than 2 seconds, preferably between 0.25 and 1 seconds, more preferably between 0.25 and 0.5 seconds. However, it is practically difficult to design and operate the PGB for lower residence times because lower residence times lead to very high gas velocities which in turn may increase the material problems incurred.

WO2010/144544 A1 discloses a method for producing synthesis gas from biomass. The document discloses solar driven refining of biomass and the lowering of the temperature after the reaction to avoid the reverse reaction by various means, for example by indirect heat exchange or by quenching with water. It is disclosed that rapid cooling e.g. between 0.1 and 10 seconds, may reduce the metal dusting phenomenon. There is no disclosure of the particular problems associated with the use of a catalytic partial oxidation reaction followed by a water gas shift (WGS) reaction, i.e. the increased corrosiveness and the need to adjust the S/G ratio before the WGS reaction. A typical temperature of less than 800° C. is disclosed as required to prevent the reverse reaction and optimize the amount of syngas.

It is thus desired to provide a process which is capable of providing syngas and reduce or avoid conditions that could promote the phenomenon of metal dusting.

SUMMARY OF THE INVENTION

In order to better address one or more of the foregoing desires, the invention presents, in one aspect, a process for producing a synthesis gas mixture, the method comprising the steps of:
(a) providing a composition comprising a hydrocarbon material;
(b) subjecting the hydrocarbon material to catalytic partial oxidation (CPO) so as to produce initial synthesis gas comprising carbon monoxide, hydrogen and carbon dioxide;
(c) adding liquid water to the initial synthesis gas obtained in (b) in an amount sufficient to obtain a synthesis gas mixture comprising $H_2O$ as the primary component.

In another aspect, the invention pertains to a process for the production of a gas mixture comprising hydrogen and carbon dioxide, the method comprising the above steps (a)-(c), and subjecting the synthesis gas mixture to
(d) a water gas shift reaction so as to react carbon monoxide with water under the formation of a gas mixture comprising hydrogen and carbon dioxide.

In a still further aspect, the invention serves to produce hydrogen by a method comprising the above steps (a)-(d), and separating the hydrogen from the gas mixture.

In yet another aspect, the invention presents a method of making urea, comprising above steps (a)-(d), removing $CO_2$ from the gas mixture comprising hydrogen and carbon dioxide, so as to obtain a gas mixture enriched in $H_2$, reacting the $H_2$-enriched gas mixture with $N_2$ so as to form ammonia, and reacting the ammonia with the removed $CO_2$ under urea-forming conditions.

In a further aspect the invention pertains to the use of liquid water for the purpose of setting the steam/gas ratio (S/G, v/v %) in a synthesis gas mixture to be subjected to a water gas shift reaction for the production of hydrogen.

In a still further aspect, the invention pertains to a plant for the production of hydrogen, said plant comprising a catalytic partial oxidation reactor and a water gas shift reactor downstream of the catalytic partial oxidation reactor, wherein an injector for water is placed between a gas outlet of the catalytic partial oxidation reactor and a gas inlet of the water gas shift reactor.

DETAILED DESCRIPTION OF THE INVENTION

Figure 1:
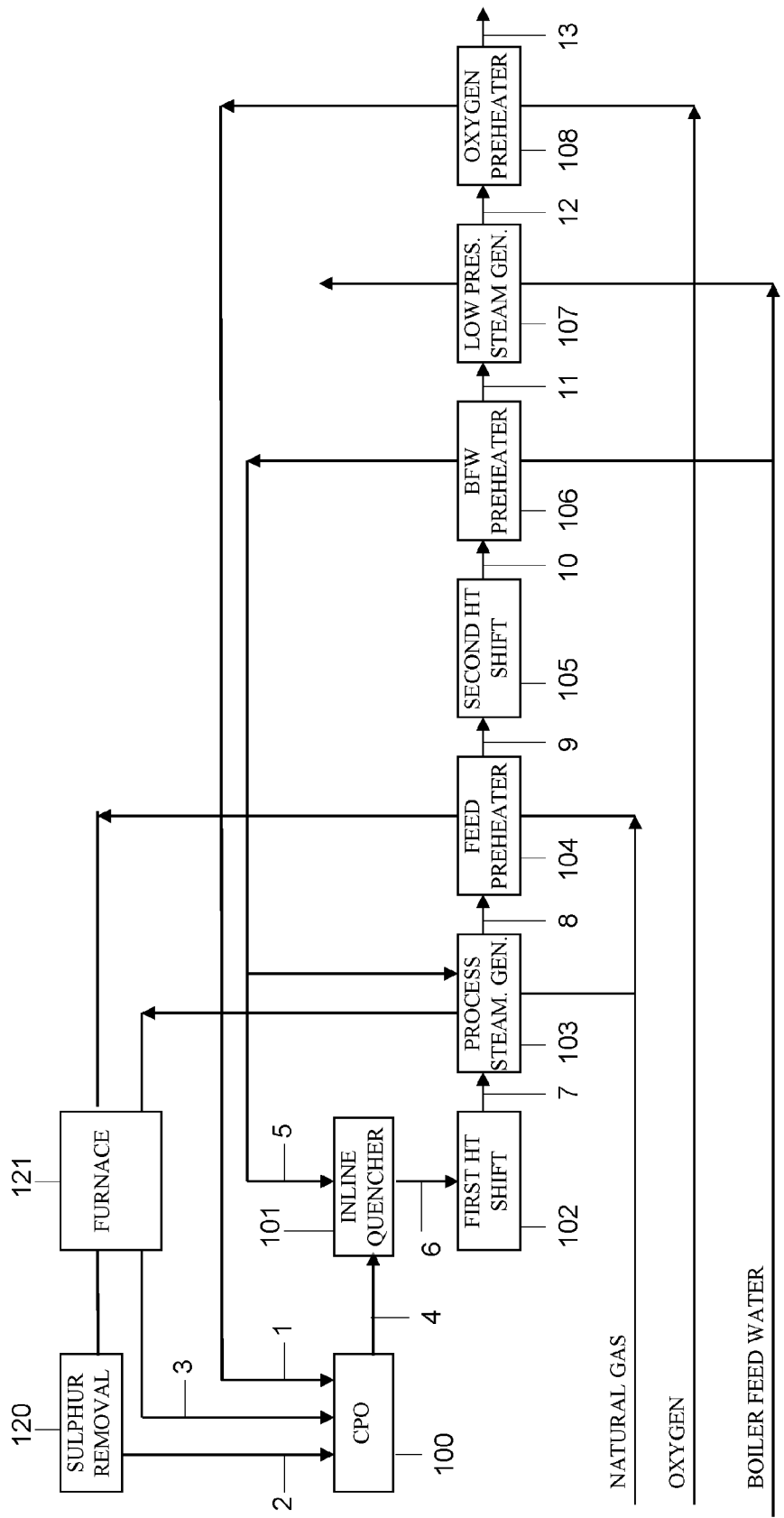
FIG. 1 depicts a process scheme illustrating one embodiment of the present invention to produce a syngas with the optimum steam to gas (S/G) ratio for the shift reaction without adding steam and eliminating the possibility to enter into the range of temperatures critical for the metal dusting phenomenon.

In a broad sense, the invention is based on the judicious insight that the addition of liquid water is capable of serving a double goal in the field of CPO syngas production. Accordingly, the water contributes to achieving the desired rapid cooling, as well as to enabling the production of a gas mixture having a more desirable composition for the water gas shift reaction.

It will be understood that the heat exchange that occurs when liquid water is added to the initial synthesis gas mixture, will result in the water to become evaporated, thus adding steam to the gas mixture. The amount of liquid water added is such, that the steam (i.e. $H_2O$ in the gas phase) becomes the primary component of the gas mixture. By "primary" it is meant that the $H_2O$ is present in relatively the highest amount.

The addition of liquid water serves to achieve a fast cooling, that in turn serves to avoid the metal dusting phenomenon which would otherwise occur in the range of 450-750° C. Further, the step of adding liquid water does not only provide an elegant way of achieving rapid cooling, it also means that, by adapting the amount of liquid water to be added, one can adapt the total composition of the gas mixture.

The hydrocarbon material can be a single hydrocarbon, a mixture of hydrocarbons, or any other composition comprising at least one hydrocarbon. Preferred sources are natural gas ($CH_4$), liquid hydrocarbons, for example naphtha or gasoline, gasification of coal, biomass, and waste-to-energy gasification facilities.

The hydrocarbon material can be in a gaseous (e.g. methane or natural gas) and/or in liquid state and also from biomass; The hydrocarbon material may be suitable for direct feed to the CPO or can be pre-treated for removal of any impurities, such as sulfur compounds, that might be present.

CPO reactors are known to the skilled person. A CPO reactor generally comprises a reaction zone, made up of a vertical cylindrically shaped steel pressure vessel lined with a refractory material. A CPO reactor typically is distinguished from an autothermal reformer reactors, as the latter comprises a burner, which a CPO generally does not.

The CPO process results in synthesis gas, or syngas, comprising CO, $CO_2$ and $H_2$.

The CPO reaction is known to the skilled person. It will generally be carried out in a catalytic partial oxidation reactor, comprising a suitable catalyst bed that serves to catalyze the partial oxidation of hydrocarbon into CO and $H_2$. It will be understood that some complete oxidation product (viz. $CO_2$) may also be formed.

The term CPO (also often referred to as SCT-CPO) is known to the skilled person. SCT-CPO refers to Short Contact Time Catalytic Partial Oxidation. The CPO reaction takes place in a reactor under the influence of a catalyst at residence times between $10^{-2}$ to $10^{-4}$ and with typical catalyst surface contact times around $10^{-6}$ $s^{-1}$. These contact time correspond to typical space velocities of 100,000 to 250,000 $hr^{-1}$ preferably 100,000 to 200,000 $hr^{-1}$. Catalysts employed for SCT-CPO comprise Ni, Pd, Pt, Rh, or Ru. The reaction takes place at catalyst surface temperatures above 950° C., preferably above 1000° C. By employing said short contact times and high catalyst surface temperatures the formation of CO his highly favoured and the formation of carbon or CO2 is suppressed. This leads to a highly favourable synthesis gas composition. A reference to CPO is (a) L. Basini, Catalysis Today 117 (2006) 384-393. Other references include (b) L. Basini, K. Aasberg-Petersen, A. Guarinoni, M. Oestberg, Catalysis Today (2001) 64, 9-20 "Catalytic Partial Oxidation of Natural Gas at Elevated Pressure and Low Residence Time"; (c) H. Hickman, L. D. Schmidt, J. Catal. 138 (1992) 267; (d) D. Hichman, L. D. Schmidt Science, 259 (1993) 343; (e) L. Basini, G. Donati WO 97/37929; (f) Sanfilippo, Domenico; Basini, Luca; Marchionna, Mario; EP-640559; (g) D. Schaddenhorst, R. J. Schoonebeek; WO 00/00426; (h) K. L. Hohn, L. D. Schmidt, S. Reyes, J. S. Freeley, WO 01/32556; (i) A. M. Gaffney, R. Songer, R. Ostwald, D. Corbin, WO 01/36323.

According to the invention, the initial synthesis gas resulting from the CPO reaction, is modified by the addition of liquid water. This results in a useful gas mixture comprising the components of the synthesis gas, and additionally $H_2O$ as the primary component. The addition of water to the initial syngas mixture is carried out preferably by a direct injection of preheated water into the gas at the outlet of the CPO reactor. By setting the proper operating conditions on the CPO reactor (oxygen/carbon, $O_2$/C, and steam/carbon, S/C, ratios) and the temperature of the heated injected water (typically Boiler Feed Water is used for this purpose), the optimum ratio, S/G, is achieved without any further addition of steam and the proper temperature at the inlet of WGS reactor without the need of installing a Process Gas Boiler (PGB) downstream of the CPO reactor. By adjusting the temperature and/or the amount of the liquid water to be added, the skilled person can relatively simply determine the desired composition and temperature of the synthesis gas mixture obtained. Put simply, at a relatively low water temperature, a lower amount of water will be required to cool the initial synthesis gas, and vice versa. The invention, in one aspect, embodies a quite unexpected phenomenon, viz. that the amount of water required to perform the cooling as well as to adjust the S/G ratio, happens to be in the range that is capable of being adjusted by adjusting the temperature of the preheated water.

This synthesis gas mixture preferably serves as an intermediate in the production of hydrogen, involving a water gas shift reaction. In that case, it is preferred that the temperature of the initial synthesis gas mixture be reduced (from a typical value such as 950° C. to 1050° C.) to below 450° C., and preferably to below 400° C. The proper temperature of water to be injected downstream the CPO reactor is preferably achieved by using heat from the syngas at the outlet of the water gas shift reactor to preheat the water.

For the purpose of producing hydrogen, the mixture is subjected to a water gas shift reaction. To this end, the mixture is routed to a water gas shift reactor (WGSR), wherein the gas mixture comprising carbon monoxide and steam is converted to hydrogen and carbon dioxide. The WGS reaction is typically carried out using either a single stage or multi stage to attain the desired degree and rate of conversion. In a multi stage process, the high temperature stage (HTS) operates at 300-450° C. and typically in the presence of an iron-based catalyst such as Fe/Cr. In the HTS the largest amount of CO is converted, usually more than 90% such as between 96 and 98%. In the following stage, medium or low temperature stage (MTS or LTS), the operating temperature is about 180-280° C. and typically a copper/zinc catalyst supported on alumina (Cu/Zn/Al) catalyst is used. In these latter stages the residual CO concentration in the outlet stream is typically as low as 0.1-0.3%.

The gas stream resulting from the WGSR contains mainly hydrogen and carbon dioxide. Optionally, hydrogen is separated from this stream by pressure swing absorption (PSA) to yield a pure hydrogen stream. Several options exist for further treatment of the gas mixture resulting from the water gas shift reaction. E.g., in order to produce hydrogen, the hydrogen can be separated from the gas mixture. It is also possible to use the method for the express production of hydrogen and carbon dioxide.

In a particular embodiment, the method is used for the production of ammonia and urea. To this end, almost all $CO_2$ is removed from the gas mixture comprising hydrogen and carbon dioxide, so as to obtain a gas mixture enriched in $H_2$. The latter is reacted with $N_2$ so as to form ammonia. This reaction is well-known, and the skilled person is familiar with production methods and plants to carry this out. The ammonia is then reacted with the removed $CO_2$ under urea-forming conditions. This reaction too is well-known, and production methods and plants are available to the skilled person. The invention thus provides a very economical way of using the components of the gas mixture obtained, in producing the important bulk chemical compound, urea. The advantage of using the above scheme instead of a conventional steam reforming process is that all $CO_2$ is present in the reaction mixture and as such can be easily removed. In a conventional steam reforming process, only part of the $CO_2$ is present in the reaction mixture, a significant amount of $CO_2$ is present in the flue gas originating from the burning of the fuel needed to supply the heat of reaction.

The invention further pertains to a plant for the production of hydrogen. In connection with the above-mentioned process embodiments, the plant comprises a catalytic partial oxidation reactor and a water gas shift reactor, downstream of the catalytic partial oxidation reactor. It will be understood that the catalytic partial oxidation reactor may comprise the conventional elements of such a reactor. These comprise, e.g., an inlet for a hydrocarbon feed, a synthesis section comprising a catalytic bed, and an outlet for synthesis gas formed. The water gas shift reactor too, will comprise its conventional elements, such as an inlet for synthesis gas, a reactor chamber, and an outlet for a resulting $H_2$-containing gas stream. In accordance with the invention, an injector for water is placed between the gas outlet of the catalytic partial oxidation reactor and the gas inlet of the water gas shift reactor. The injector may be in the form of a separate quenching unit, comprising a quenching chamber provided with a device to inject water. It may also be provided as an injector into a piping system.

In a preferred embodiment, a heater, typically a heat exchanger, is added to the injector, preferably upstream thereof, so as to preheat the water before it is used.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" or "an", "the", this includes a plural of that noun unless something else is specifically stated. All ratios such as steam/gas (S/G), steam/carbon (S/C) and oxygen/carbon (O/C) are expressed as volume ratios (v/v)

DETAILED DESCRIPTION OF THE FIGURES

In FIG. 1, a first embodiment of the present invention is illustrated in a schematic form.

FIG. 1 shows the block diagram of the process with the following sections:
100, CPO section;
101, quenching section;
102, first HTS section;
103, process steam generation section;
104, feed preheater;
105, second HTS section;
106, BFW preheater section
107, low pressure steam generation section
108, oxygen preheater section;
120, sulfur removal reactor;
121, furnace.

To the syngas stream from CPO reactor, 100, water is added in 101 to cool the syngas temperature to 320-350° C. which represents a proper temperature to carry out the high temperature water gas shift reaction and which is outside the critical temperature range for metal dusting phenomenon. Unless indicated otherwise all percentages referred to are vol. %.

The synthesis gas exits the water quencher, 101, with a product containing about 32.7% of $H_2$, 0.5% of unconverted $CH_4$, 2.6% of $CO_2$, 16.7% CO and 47.5% of $H_2O$.

Due to water addition, the S/G ratio in the stream 6 rises to 0.9-1, which represents the optimum value for the subsequent shift.

In the invention, as a result of the judicious step serving to control the amount of the added water, the mixture entering the WGS reactor has the correct composition for an optimal reaction. This refers to step (c), according to which liquid water is added in an amount sufficient to obtain a synthesis gas mixture comprising, in deviation from the state of the art, $H_2O$ as the component that is present in the mixture in the highest amount relative to the other components, i.e., as the primary component. Preferably, the amount of liquid water injected is such that it comprises 30 to 60 percent by volume relative to the total mixture.

Preferably, in addition to controlling the amount of the added water, also the temperature of the added water is controlled so as to be in a range of from 120° C. to 250° C.

As a result, the mixture entering the WGS reactor has the correct composition and temperature for an optimal reaction.

In addition the amount of energy needed after the WGS to cool will be minimized. The optimum Steam to Gas ratio (S/G) of the mixture entering the WGS reactor is between 0.75 and 1.1, preferably between 0.9 and 1.0.

In the reactor 102, a first high temperature shift reactor, a substantial portion of the CO present in the stream 6 is converted into $CO_2+H_2$.

Downstream to reactor 102 and before the second temperature shift reactor, 105, a process steam generation, 103, to produce the steam necessary for the CPO reactor and feed preheater 104 installed to preheat the natural gas feed, flowing through the sulfur removal reactor 120.

Stream 9 enters into the second shift reactor, 105, to convert remaining CO in the $H_2$ product.

In the outlet stream, 10, at a temperature of 345° C., residual CO is 1.8%.

The water stream preheater 106 will heat the water to between 150° C. and 250° C. Typical pressures are between 10 and 40 barg preferably between 10 to 30 barg, for example 20 barg. The low pressure steam generation, 107, and oxygen preheater, 108, are placed downstream of reactor 105 to cool down the syngas product.

In one embodiment the gas at the exit of the CPO reactor is cooled in less than 100 ms, preferably the gas is cooled in less than 50 ms, more preferably less than 30 ms, for example 20 ms.

In the scheme is included a furnace, 121, to raise the temperatures of the steam and of the feed at the values desired at the inlet of CPO reactor.

Figure 2:
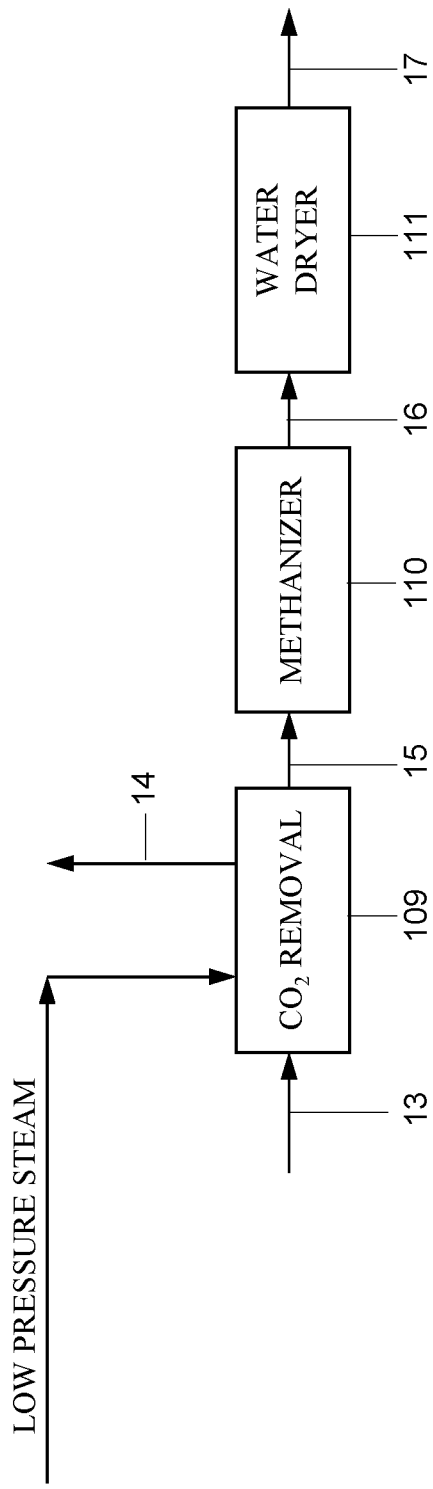
FIG. 2 presents a process scheme illustrating a second embodiment of the present invention, wherein the syngas serves to make a stream of pure $H_2$.

Referring now to FIG. 2, a second embodiment of the present invention is illustrated in schematic form.

For simplicity, units and streams, FIG. 2 has in common with FIG. 1 have retained the unit or stream number of FIG. 1 so it shows only the following section.

109, $CO_2$ removal section;
110, methanizer reactor section;
111, water dryer section.

The shifted gas, 10, is processed in acid gas unit 109.

In acid gas stream, 13, the $CO_2$ is separated from the syngas product. Stream 14 consists of $CO_2$ removed.

The raw $H_2$ stream, 15, is routed in reactor, 110, where CO is converted in $CH_4$ and in reactor 111, where water is removed.

The $H_2$ product, 17, has purity of 93.7% and can be used for applications which do not require high purity $H_2$. If desired the $H_2$ stream can be further purified with a pressure swing absorption (PSA) unit (not shown) or in case a $CO_2$ separated stream is not required instead of steps 109, 110 or 111.

The above illustrated embodiments are intended to serve as simplified schematic diagrams of potential embodiments of the present invention. One of ordinary skill in the art of chemical engineering should understand and appreciate the specific details of any particular embodiment may be different and will depend upon the locations and needs of the scheme under consideration.

All alternatives scheme capable of achieving the present invention are considered to be within the capabilities of a person having skill in the art and thus within the scope of the present invention.

The invention claimed is:

1. A process for producing a synthesis gas mixture, the method comprising the steps of:
    (a) providing a hydrocarbon material which is gas and/or liquid;
    (b) subjecting the hydrocarbon material to catalytic partial oxidation (CPO) so as to produce a first synthesis gas mixture comprising carbon monoxide, hydrogen and carbon dioxide;
    (c) adding liquid water to the first synthesis gas mixture obtained in (b) in an amount such that said liquid water is completely vaporized and said liquid water, without further addition of steam, results in a second synthesis gas mixture comprising vaporized water in an amount appropriate to conduct a water-gas shift reaction, said vaporized water resulting from said adding being present at 30 to 60 percent by volume relative to the total components of the second synthesis gas mixture; and
    no further steam is added in this step (c); and
    wherein the liquid water is preheated to a temperature of 120 to 250° C., and directly injected at 10-40 barg pressure and the addition of the liquid water results in cooling of the second synthesis gas mixture in less than 50 msec to a temperature appropriate to conduct a water-gas shift reaction.

2. A process for the production of a gas mixture comprising hydrogen and carbon dioxide, the method comprising the steps (a)-(c) as defined in claim 1, and subjecting the second synthesis gas mixture to
    (d) a water gas shift reaction so as to react carbon monoxide with water to form a gas mixture comprising hydrogen and carbon dioxide.

3. A process for the production of hydrogen comprising the steps (a)-(d) as defined in claim 2, and separating the hydrogen from the gas mixture.

4. A process for the production of urea, comprising steps (a)-(d) as defined in claim 2, removing $CO_2$ from the gas mixture comprising hydrogen and carbon dioxide, and using the obtained $CO_2$ in the preparation of urea.

5. The process according to claim 2, further comprising removing $CO_2$ from the gas mixture comprising hydrogen and carbon dioxide obtained by performing steps (a)-(d), so as to obtain a gas mixture enriched in $H_2$.

6. The process of claim 2 wherein in step (c) the synthesis gas mixture is cooled from 950°-1050° C. to below 400° C. and the second synthesis gas mixture has steam/gas (S/G) ratio of 0.9-1.0.

* * * * *